United States Patent
Richter et al.

(10) Patent No.: US 8,761,453 B2
(45) Date of Patent: Jun. 24, 2014

(54) METHOD AND DEVICE FOR THE SURFACE INSPECTION OF STRIP PIECES

(75) Inventors: Hans-Peter Richter, Friedewald (DE); Dirk Achenbach, Erndtebrueck (DE)

(73) Assignee: SMS Siemag AG, Duesseldorf (DE)

( * ) Notice: Subject to any disclaimer, the term of this patent is extended or adjusted under 35 U.S.C. 154(b) by 0 days.

(21) Appl. No.: 13/996,139

(22) PCT Filed: Nov. 24, 2011

(86) PCT No.: PCT/EP2011/070878
§ 371 (c)(1),
(2), (4) Date: Jul. 31, 2013

(87) PCT Pub. No.: WO2012/084399
PCT Pub. Date: Jun. 28, 2012

(65) Prior Publication Data
US 2013/0322734 A1    Dec. 5, 2013

(30) Foreign Application Priority Data

Dec. 21, 2010 (DE) .......................... 10 2010 055 340
Sep. 26, 2011 (DE) .......................... 10 2011 083 405

(51) Int. Cl.
*G06K 9/00* (2006.01)
(52) U.S. Cl.
USPC .......................................... 382/108; 382/141
(58) Field of Classification Search
CPC ............... G06T 7/0002; G06T 7/0004; G06T 2207/30136; B21B 38/00; B65H 43/08; G01N 21/86; G01N 21/88; G01N 21/8803; G01N 21/89; G01N 21/892; G01N 21/8922; G01N 2021/8918; G01N 2012/892
USPC .......... 382/108, 141, 152, 284; 356/429, 430, 356/431, 237.1, 237.2; 250/548, 559.01, 250/559.05, 559.07, 559.08; 348/125, 128
See application file for complete search history.

(56) References Cited

U.S. PATENT DOCUMENTS

| | | | |
|---|---|---|---|
| 3,780,882 A | 12/1973 | Wagner | 214/1 QA |
| 3,812,373 A * | 5/1974 | Hosoe et al. | 250/562 |
| 3,980,109 A | 9/1976 | Trueman et al. | 141/71 |
| 4,982,600 A * | 1/1991 | Kiso et al. | 73/104 |

(Continued)

FOREIGN PATENT DOCUMENTS

| | | | | |
|---|---|---|---|---|
| DE | 2165936 A | 7/1973 | ............. | B21B 39/22 |
| JP | 2000-254725 A | 9/2000 | ............. | B21C 47/00 |
| JP | 2006-105791 A | 4/2006 | ............. | G01N 21/892 |

*Primary Examiner* — Andrew W Johns
(74) *Attorney, Agent, or Firm* — Abelman, Frayne & Schwab

(57) ABSTRACT

The invention relates to a method for the surface inspection of strip pieces (120). The invention further relates to a device for carrying out the method. The method according to the invention comprises the following steps: cutting off the strip pieces (120) from a metal strip (210), wherein the strip pieces (120) comprise a length less than twice the circumference of a work roll (230) by means of which the metal strip (210) has previously been rolled; automatically checking the upper and/or lower side of the cut-off strip pieces (120) with the aid of a camera system (150) and an analysis unit (300) in regard to any periodic types of faults that may be present and caused by the work roll; ending the surface inspection process if periodically occurring types of faults are detected, or; feeding the cut-off strip pieces (120) to a strip inspection unit (140) for checking by means of inspection personnel for non-periodic types of faults if no periodic types of faults had previously been detected.

6 Claims, 2 Drawing Sheets

(56) References Cited

U.S. PATENT DOCUMENTS

| | | | |
|---|---|---|---|
| 6,778,694 B1* | 8/2004 | Alexandre | 382/141 |
| 8,439,625 B2 | 5/2013 | Pass et al. | 414/759 |
| 2006/0165513 A1 | 7/2006 | Tiepelman et al. | 414/759 |
| 2009/0208093 A1* | 8/2009 | Mauuary | 382/152 |
| 2011/0040499 A1* | 2/2011 | Koshihara et al. | 702/35 |

* cited by examiner

METHOD AND DEVICE FOR THE SURFACE INSPECTION OF STRIP PIECES

The invention relates to a method for the surface inspection of strip pieces.

In the prior art, the rolled products are checked on their upper sides for rolling defects for quality control, following a rolling process. This quality control is performed in downstream lines or devices. Strip pieces are normally cut off from a metal strip and are transferred to a strip inspection unit. The strip inspection is performed in the strip inspection unit visually during the check by inspection personnel. Impression marks and indentations which frequently occur periodically amongst other things, are detected. These periodic occurring defects point to a defective roll surface and indicate that the work roll must be changed. This roll change should be carried out as soon as possible, so that the work roll with the defect on its surface can no longer produce further rejects. In order to detect periodicity, these strip pieces must be cut to a length that corresponds to at least two complete roll circumferences.

To detect additional defects in the surface structures of the strip pieces, the strip surface is manually ground in the strip inspection unit. A turnaround device makes it possible for the inspection personnel to check the upper side and the lower side of the strip. For this purpose, the cut strip pieces are held in a clamping device and are tilted such that the surface can be inspected by the operators also on the other side of the rolled product. After the quality control, the strip piece is placed onto a stack of strips, removed and disposed of, if necessary.

Surface inspection systems are presented in the technical articles "Surface inspection system with defect classification, Iron and Steel Engineer, May 1990" and "Effizienzoptimierung in der Flachstahlherstellung durch Oberflächeninspektion, Stahl und Eisen, Dezember 2001" *[Efficiency optimization in the production of flat steel by surface inspection, Stahl und Eisen, December* 2001], which detect and analyze defects such as scratches or roll defects on the surface of a strip by using sensors or camera systems, and analyze them electronically.

Devices and corresponding methods for the automatic detection of surface defects in products from continuous casting and from rolling are also discussed in the printed specifications EP 0 880 023, EP 1 972 930 and DE 32 22 753.

Since many types of defects only become visible by grinding the strip surface, the benefit of automatic surface inspection is currently rather limited. For this reason, the strip inspection system in which the analysis is also performed visually by the operators, is therefore in the focus of optimization. EP 1 590 106 presents an inspection system which offers the inspection personnel optimum ergonomics when grinding the strip pieces which therefore improves the performance options and optimizes the working conditions.

A disadvantage of the known surface inspection systems is however, that the strip pieces must have a constant length of at least two full roll circumferences, in tandem mills 6000 mm, for example, to detect periodic roll defects. Because of the geometric dimensions of the strip pieces this results in the necessary space required for the strip inspection unit. The handling of the strip pieces is also complicated and time intensive because of their length. The conveyance also takes more time. A further disadvantage is that no result of the surface inspection is available for a running strip, since it can only be determined after a delay. This also means that the work roll can be replaced only after a corresponding delay, while further metal strip, for example several coils, will be processed with the defective work roll. The wastage of rolled metal strips with a defective surface produced in this way is immense and cost-intensive.

The object of the invention is to improve a known method and a known device for the inspection of strip surfaces to the extent that simple, flexible and faster handling of the strip pieces to be inspected is possible.

The problem presented is solved by the method characterized in that the following steps are performed: cutting off the strip pieces from a metal strip, wherein the strip pieces comprise a length smaller than twice the circumference of a work roll which was used to roll the metal strip earlier, the automatic inspection of the upper and/or lower side of the cut-off strip pieces with the aid of a camera system and an analysis unit with respect to any potential types of periodic defects which may be present that were caused by the work roll and terminating the method of the surface inspection, if periodic types of defects occur and are detected, or by feeding the cut-off strip pieces to a strip inspection unit for a check by inspection personnel for non-periodic types of defects, if no periodic types of defects were detected previously.

Initial Rolling:

In this application, the term initial rolling is to be understood as the first run of the metal strip through the rolling mill until such time that the work rolls for rolling the metal strips are adjusted correctly.

Beginning of the Strip:

The beginning of a metal strip to be rolled will not be rolled to the desired thickness by the work rolls, because this beginning of the strip has already run through the plant once before the work rolls were correctly adjusted. This first section of the strip is cut off and disposed of. The newly created beginning of the strip that the metal strip now has because the first section of the strip was cut off, has preferably already been rolled by the work rolls to the desired thickness, and will now be cut off from the rolled metal strip to check for types of defects. Because the method according to the invention works with cut-off strip pieces, the length of which is shorter than twice the length of the circumference of the work roll, this results in the necessity for cutting off multiple beginnings of strip from the same metal strip until such time that all of the cut-off strip pieces, when placed consecutively, result in a fragmented strip piece with a length that is larger than twice the circumferential length of the work roll. In terms of the invention, the feature "beginning of the strip" is to be understood such that several strip pieces having the desired thickness are cut off from the respective beginning of the one metal strip as often as necessary.

That the strip pieces with a length smaller than twice the circumference of the work roll which was used to roll the metal strip earlier are cut off, offers the advantage that the strip pieces are shorter than in the prior art. The handling of the strip pieces by the inspection personnel during a visual inspection can therefore be done easier and less problematic. The stacking and conveying becomes also significantly more efficient, because a larger number of cut-off strip pieces can be stacked and removed than strip pieces which have longer dimensions.

The automatic inspection of the upper and/or lower side of the cut-off strip pieces is advantageously carried out with the aid of a camera system or an analysis unit as regards any potentially present periodic types of defects caused by the work roll. At the same time this has the advantage of detecting the periodic surface defects as quickly as possible and the ability of replacing the work roll with the defective roll marks in a timely manner. Then the result of the inspection for periodic types of defects is known still while the metal strip from the beginning of which the strip piece to be inspected was cut off is being rolled. The inspection personnel in the strip inspection unit can therefore concentrate on the types of defects which do not occur periodically, shortening the inspection period. The camera system will advantageously inspect the strip pieces not directly at the discharge side of the rolling mill, because unfavorable conditions of vibility prevail at that location due to fumes, vapor from emulsions, or other contamination. Instead, both the automatic check for periodic types of defects as well as the visual inspection for non-periodic types of defects is done by the inspection personnel away from the line. The visual conditions for the camera system and the inspection personnel are significantly better there, and the rolling process of the metal strip can continue meanwhile.

Advantageously, the method of inspecting the surface is stopped immediately, if periodic types of defects which occur are detected. The entire process of checking in the strip inspection unit is then no longer necessary, and costs for time and transferring the defective strip piece to the strip inspection unit can be conserved, since the strip piece is disposed of directly.

Advantageously, the cut-off strip pieces are fed to a strip inspection unit for checking by the inspection personnel for non-periodic types of defects only, if no periodic type of defect was detected. As a result, the workload for the inspection personnel will be reduced and will work faster and get tired later, and will therefore be more efficient.

According to a first embodiment, the strip pieces having a length of 10% to 85% of twice the circumference of the work roll are preferably cut off from the metal strip at between 10% to 40% of twice the circumference of the work roll. This will advantageously produce faster and easier handling during further processing of the strip pieces. The conveyance with the forklift is advantageously more flexible, because approximately 150 strip pieces can be loaded at a time, depending upon the thickness of the strip. That also means that the further processing will be more cost-effective, if the existing mechanical components, such as a forklift or scrap skips can be used.

The periodic types of defects will advantageously be detected automatically with the aid of a camera system, and in the event of a defect will facilitate a timely roll replacement, thus minimizing the wastage of metal strip and having the ability to produce more cost-effectively.

The cut-off strip pieces will advantageously be detected individually by the camera system and the individual pictures resulting therefrom will subsequently be electronically assembled into one complete picture by the analysis unit, which will then represent a continuous strip piece having a length of at least twice the circumference of the work roll. Subsequently, the complete picture will be checked automatically by the analysis unit with respect to any potentially existing periodic types of defects. This will result in the advantage that in spite of short strip pieces (with a length less than twice the circumference of the roll) an electronic total picture of a long strip piece will be produced that corresponds to at least twice the full circumference of the work roll. The periodic types of defects can also be electronically/automatically identified, although the actual geometric dimensions of the cut-off strip pieces would not permit this to be done by a direct observer. Advantageously, the length of the strip pieces has been decoupled from the necessary length to be inspected.

Advantageously, the periodic types of defects detected will be displayed on a monitor and/or recorded, classified, stored and/or printed, by an analysis unit. The occurrence of the periodic defects is therefore not only visible, but can also be assigned and substantiated for purposes of quality assurance, and typical types of defects will be classified automatically. The periodic types of defects will advantageously already be displayed for the running strip, for example on a monitor in the main control center, and the operator can stop the rolling process immediately.

During the operation of a mill train, following the initial rolling of a metal strip, the method as taught by the invention for surface inspection will advatageously be performed such that strip pieces are cut off from the beginning of strips and/or the end of strips of the metal strip that has been rolled at least once, and that the mill train is switched off immediately as soon as a periodically occurring defect type is detected during the automatic check. Advantageously, only a portion of the metal strip has been rolled while the periodically occurring type of defect is detected. This offers the advantage that the defective work roll can be replaced immediately without that additional defective metal strip is rolled. Advantageously, the notice for changing the work role with a defective surface will be shown immediately at the respective location, thereby keeping the delivery of rejects as low as possible. A change that is performed in a timely manner moreover has the advantage that the work roll itself is protected from being destroyed. The incurring losses can advantageously be kept small both with the metal strip to be rolled or on the work roll, by being able to switch off the plant very quickly.

The above-mentioned problem is moreover solved by a device for the surface inspection of strip pieces, pursuant to the invention.

The advantages of the device correspond to the advantages mentioned above with reference to the method according to the invention.

Further advantageous embodiments of the device and the method of the invention are stated in the sub-claims.

Two figures are attached to the specification, wherein

Figure 1:
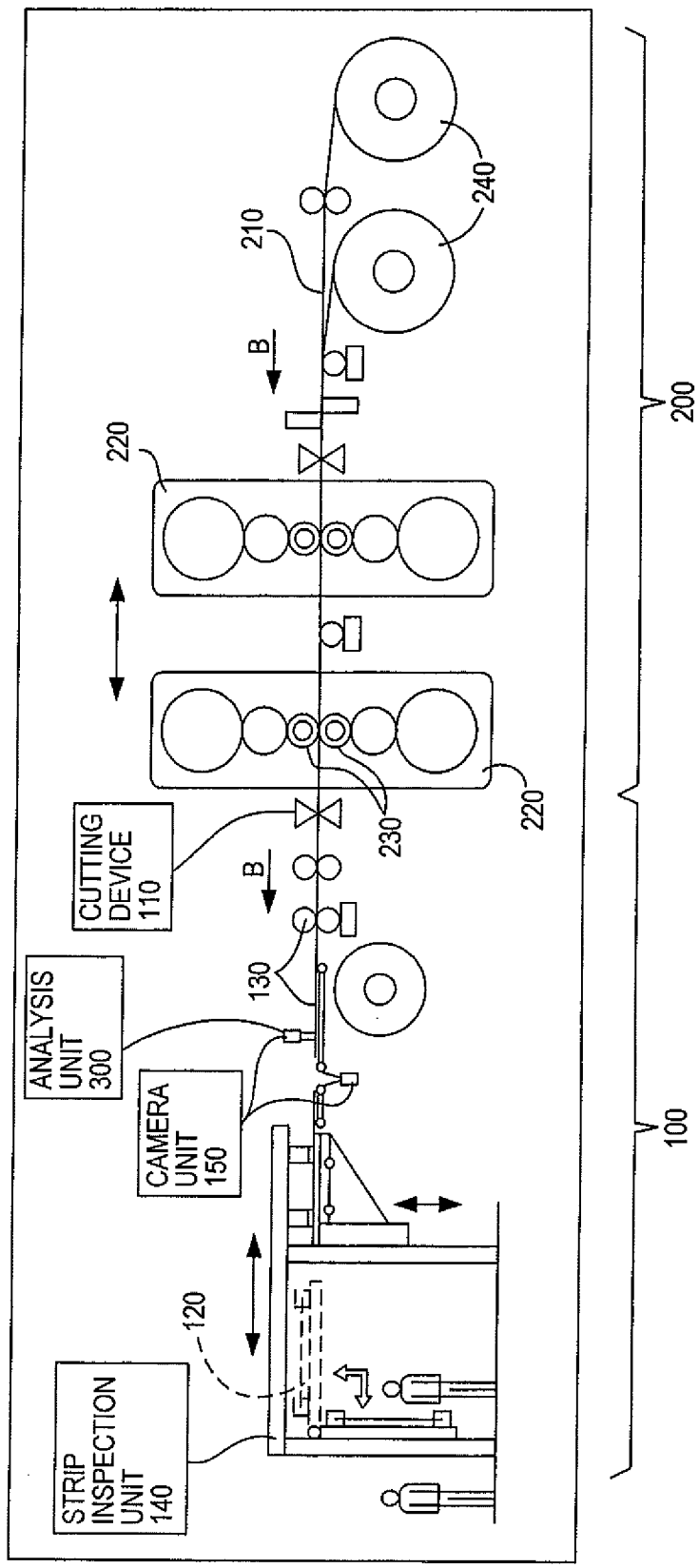
FIG. 1 shows a device for surface inspection.

FIG. 1 illustrates the device 100 according to the invention following immediately behind a mill train 200. A metal strip 210 is fed from a coil 240 to a rolling mill stand 220 in the direction B of processing the strip. The beginning of the metal strip 210 is fed through the rolling mill stand 220 and work rolls 230 are adjusted subsequently so that the metal strip can be rolled. The beginning of the strip, which is not yet subjected to the rolling, is cut off and disposed of. By cutting off the first beginning of the strip, this results in that the metal strip 210 has a new beginning of the strip, which was already previously rolled by the work rolls. Following this initial rolling of the metal strip 210, a cutting device 110 cuts off strip pieces 120/beginnings of strip with a length smaller than twice the circumference of the work roll 230 from the metal strip 210. The length below this limit is free. If the strip pieces 120 required for the surface inspection were cut off, the metal strip is fed to the wind-on reel and is being rolled to the required thickness by the work rolls 230. Already while the metal strip is rolled and wound up, the previously cut-off strip pieces 120 are recorded by a camera system 150, so that a result of the check is available in a timely manner. Before reaching the end of the actually rolled metal strip 210, strip pieces 120 are cut off from the end of the strip, which are also used for purposes of surface inspection, and the rolling process begins anew with a new coil 240.

For the purpose of checking the strip pieces 120, these can be the beginnings or the ends of strip; after different types of defects, the conveyance of the cut-off strip pieces 120 is done with the aid of a transportation device 130. Before the cut-off strip pieces 120 are fed to a strip inspection unit 140, the camera system 150 takes a picture of the surface of the strip pieces 120. For that purpose, at least one surface inspection camera is arranged above and/or below the strip pieces 120. In order to take a picture with the camera system 150, the length of the cut-off strip pieces 120 is not important, because a total length of the strip pieces 120 with at least twice the length of the circumference of the work rolls 230 can be generated electronically from a plurality of picture images, which is needed for the analysis of any periodic surface defects which may have occurred.

Figure 2:
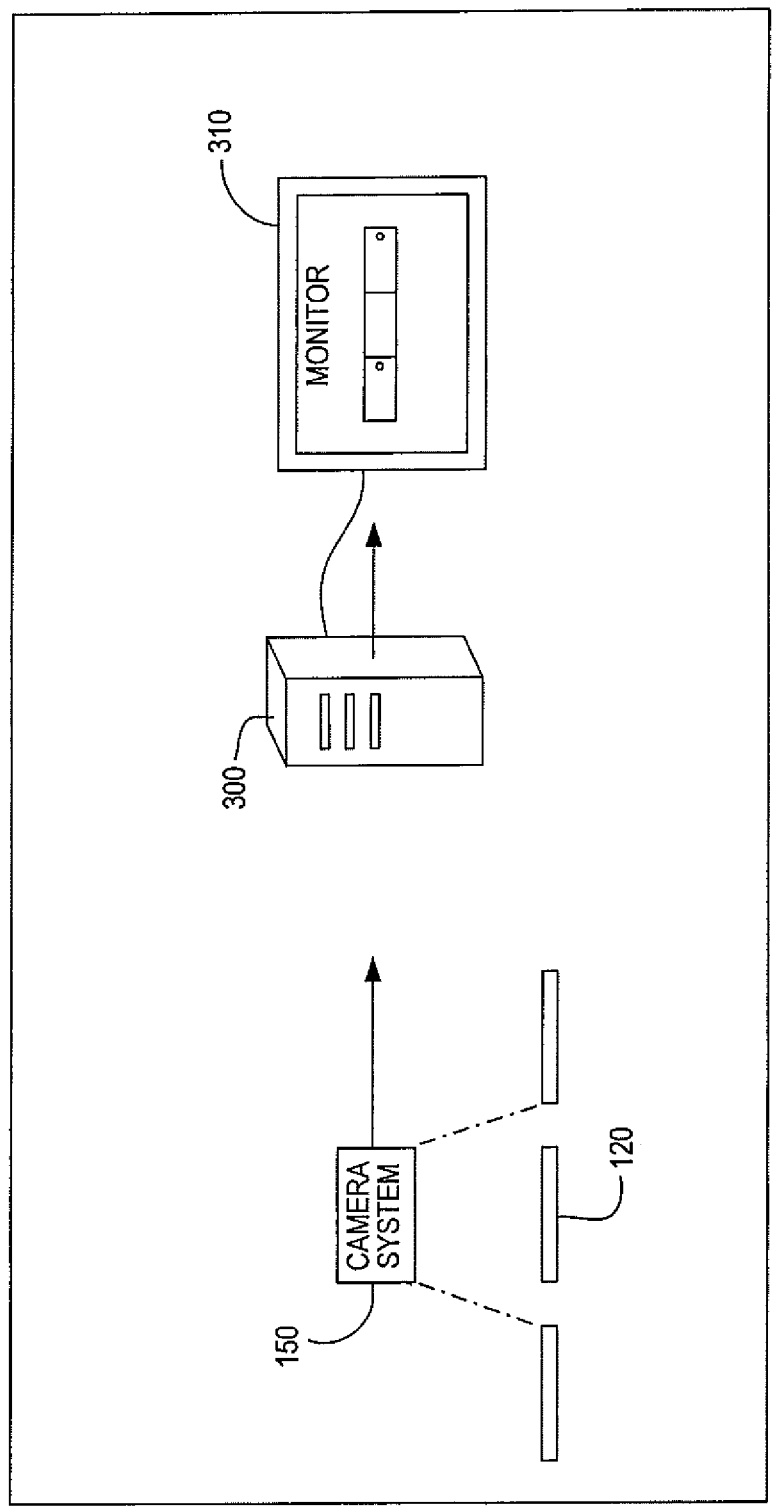
FIG. 2 shows schematically assembling of individual images in a single image.

As discussed, FIG. 2 shows assembling of individual images into a single image. In FIG. 2, the camera system 150 detects individual images of strip pieces 120, with the defects in the surface of the work roll being represented by spots in individual images 1 and 3. The individual images transmitted by the camera system 150, are assembled in the analysis unit 300, with the distance between the spots corresponding exactly to one circumference of the work roll, and are displayed on a monitor 310.

The exposure taken from the strip surface, that is pictures of the upper and lower side of the strip pieces 120, are forwarded to an analysis unit 300 which is downstream of the camera system 150. The analysis unit 300 is designed such that it detects and analyzes roll marks in the form of periodic surface defects of the strip pieces 120. After detecting the defect/segmentation and the extraction of the feature, the marks on the strip which are recurring with the circumference of the roll are stored, classified, and printed and are immediately displayed as a message on a monitor with a notice that the roll must be replaced, for example. This can be displayed at the main control console, for example. Because of the camera system 150 and the analysis unit 300, the periodic surface defects of the strip pieces 120, i.e. defects which can be seen in the circumference of the work roll 230, are automatically recorded and analyzed in a timely manner. In a timely manner means in this context that the rolling process can then be stopped immediately without delay.

If no periodic types of defects were detected, the strip piece arrives in the strip inspection unit 140. The inspection personnel there can then merely concentrate on the non-periodic surface defects of the strip pieces 120. In order to detect surface structures, the strip pieces 120 are ground by the inspection personnel in the strip inspection unit 140. For this purpose, the strip pieces 120 are held in a clamping device and are tilted. A visual inspection is performed in this position. After this visual inspection, the strip piece 120 is tilted back into the starting position and is placed onto a stack of strips. Once the stack of strips is full, the stack is lowered and strapped together, if necessary. The conveying, which is not represented here, is preferably done with a forklift. Strapping the stack with strapping tape is not provided for. For a sensible method of conveyance, the number of the strip pieces 120 is preferably approximately 150 strip pieces, which depends on the transportation capacity of the forklift. Alternatively, the disposal can be done in a scrap skip, for example.

If non-periodical types of defects are detected, the mill stand can preferably also be switched off, to stop the production of further rejects.

LIST OF REFERENCE SYMBOLS

100 Device
110 Cutting device
120 Strip pieces
130 Transportation device
140 Strip inspection unit
150 Camera system
200 Mill train
210 Metal strip
220 Mill stand
230 Work rolls
240 Coil
300 Analysis unit
B Processing direction

The invention claimed is:

1. A method of surface inspection of strip pieces (120) cut from a metal strip (210),
    characterized in that
    the strip pieces (120) have a length less than twice a circumference of a work roll (230) with which the metal strip (210) was rolled previously;
    upper and/or lower side of the cut-off strip pieces (120) is automatically checked with the aid of a camera system (150) and an analysis unit (300) in regard to any periodic types of defects that may be present which were caused by the work roll;
    the surface inspection process ends if periodically occurring types of defects are detected, or;
    the cut-off strip pieces (120) are fed to a strip inspection unit (140) for checking by inspection personnel for non-periodic types of defects if no periodic types of defects were detected previously.

2. The method according to claim 1,
    characterized in that
    the strip pieces (120) with a length of 10% to 85% of twice the circumference of the work roll (230) are cut off from the metal strip (210).

3. The method according to claim 1,
    characterized in that
    the cut-off strip pieces (120) are individually recorded by the camera system (150); and
    that the individual images resulting therefrom are subsequently electronically assembled by the analysis unit (300) into a single image, which represents a contiguous strip piece having a length of at least twice the circumference of the work roll (230), and
    that the automatic checking of the single image is performed by the analysis unit (300) with regard to any defects which may potentially be present.

4. The method according claim 1,
    characterized in that
    the captured periodic types of defects are displayed on a monitor and/or are recorded, classified, stored and/or printed by the analysis unit (300).

5. The method according to claim 1,
    characterized in that
    the strip pieces with a length of 10% to 40% of twice the circumference of the work roll (23) are cut off from the metal strip (210).

6. The method of operating a mill train (200), comprising the following steps:
    initial rolling of a metal strip (210), and
    implementing the method of surface inspection of strip pieces (120) cut from a metal strip (210) and which is characterized in that;
    the strip pieces (120) have a length less than twice a circumference of a work roll (230) with which the metal strip (210) was rolled previously;
    upper and/or lower side of the cut-off strip pieces (120) is automatically checked with the aid of a camera system (150) and an analysis unit (300) in regard to any periodic types of defects that may be present which were caused by the work roll;

the surface inspection process ends if periodically occurring types of defects are detected, or;

the cut-off strip pieces (120) are fed to a strip inspection unit (140) for checking by inspection personnel for non-periodic types of defects if no periodic types of defects were detected previously, wherein strip pieces (120) are cut off as strip beginnings and/or strip ends from the metal strip (210) which has been rolled at least once previously, and the mill train (200) is switched off immediately as soon as a periodic occurring type of defect is detected during the automatic check.

\* \* \* \* \*